United States Patent [19]

Mundschenk

[11] Patent Number: 5,989,857
[45] Date of Patent: Nov. 23, 1999

[54] POLYPEPTIDE COMPOSITIONS AND METHODS

[75] Inventor: David D. Mundschenk, Dania, Fla.

[73] Assignee: PhyloMed Corporation, Plantation, Fla.

[21] Appl. No.: 08/908,212

[22] Filed: Aug. 7, 1997

Related U.S. Application Data

[63] Continuation of application No. 08/644,399, May 10, 1996, abandoned.
[51] Int. Cl.$^6$ .............................. C12N 15/81; C12N 9/00; A61K 38/16; C07K 14/46
[52] U.S. Cl. ........................ 435/69.1; 435/183; 530/234; 530/350; 514/2
[58] Field of Search .................................. 435/69.1, 184, 435/252.3, 320.1, 254.23, 183; 530/234, 350; 536/23.1; 514/2

[56] References Cited

U.S. PATENT DOCUMENTS

| | | | |
|---|---|---|---|
| 3,888,977 | 6/1975 | Sanders | 435/5 |
| 4,126,676 | 11/1978 | Sanders | 424/542 |
| 4,162,303 | 7/1979 | Sanders | 424/542 |
| 5,002,876 | 3/1991 | Sreekrishna et al. | 435/69.5 |
| 5,165,927 | 11/1992 | Kaslow | 424/92 |
| 5,389,540 | 2/1995 | Makoff et al. | 435/69.3 |

OTHER PUBLICATIONS

Thurberg, F. P., in Aquatic Applications of Ozone, Blogoslawski, W. J., et al., Eds., "Inactivation of red–tide toxins by ozone treatment", pp. 50–58, International Ozone Institute, Pubs., 1975.

Menzel, D. B., Archives of Environmental Health, vol. 23, "Oxidation of biologically active reducing substances by ozone", pp. 149–152, 1971.

Thorsen et al (1979) J. Appl. Polymer Sci 24:523–546 "Wool Shrinkage Control and Surface Modification by Ozone".

Database on CAPLUS, "Oxidation of biologically active reducing substances by ozone", Menzel, D.B. Environ. Health, Aug. 1971, vol. 23, No. 2, pp. 149–153. Abstract only.

Chang, C., "The role of an invariant tryptophan residue in x–bungarotoxin and cobrotoxin", European Journal of Biochemistry, vol. 193(2) (1990).

Van Der Zee, J., "Toxic effects of ozone on murine L929 fibroblasts", Biochem. J., 242:707–712 (1987).

"Cloning, Characterization, and Expression of Animal Toxin Genes for Vaccine Development", L.A. Smith, J. Toxicol.–Toxin Reviews, 9(2), 243–283 (1990).

"The Use of Sanders Neurotoxoid I (Modified Snake Venom) in the Treatment of Recurrent Herpes Simplex of the Cornea: Progress Report", Clark, W.B., et al., Southern Medical Journal 55(9):947–951 (1962).

"Foreign Gene Expression in Yeast: a Review", Romanos, et al., Yeast, 8:442–433 (1992).

"Yeast Systems for the Commerical Production of Heterologous Proteins", Buckholz, et al., Bio/Technology 9:1067–1072 (1991).

"You–Prime cDNA Synthesis Kit Instructions", Pharmacia LKB Biotechnology (1989).

Stratagene (LaJolla, CA) (Catalog #236211, "Predigested Lambda ZAP II/EcoR1 Cloning Kit") (1989).

"T7 Sequencing Kit Instructions", Pharmacia LKB Biotechnology (1990).

EcoR I (see Gibco product insert for EcoR I catalog #15202–013, restriction enzyme assay for EcoR I (1994).

T4 DNA Ligase (see insert materials, Gibco BRL, Cat. # 5224SC, T4 DNA Ligase) (1992).

"Wizards Maxipreps DNA Purification System", Promega (1994).

Phillips Petroleum Company and compiled in "Pichia Expression Kit—A Manual of Methods for Expression of Recombinant Proteins in *Pichia pastoris*", which was prepared by Invitrogen and accompanies their expression kit having catalog # K1710–01.

*Primary Examiner*—Ponnathapura Achutamurthy
*Assistant Examiner*—William W. Moore
*Attorney, Agent, or Firm*—Fredrikson & Bryon, P.A.

[57] ABSTRACT

A method of preparing a bioactive polypeptide in a stable, inactivated form, the method comprising the step of treating the polypeptide with ozonated water in order to oxidize and/or stabilize the cysteine residues, and in turn, prevent the formation of disulfide bridges necessary for bioactivity. The method can involve the use of ozonated water to both oxidize the disulfide bridges in a bioactive polypeptide, and to then stabilize the resultant cysteine residues. Optionally, and preferably, the method can involve the use of ozonated water to stabilize the cysteine residues, and thereby prevent the formation of disulfide bridges, in a polypeptide produced by recombinant means in a manner that allows the polypeptide to be recovered with the disulfide bridges unformed.

10 Claims, No Drawings

POLYPEPTIDE COMPOSITIONS AND METHODS

This application is a continuation of application Ser. No. 08/644,399, filed May 10, 1996 and now abandoned.

FIELD OF THE INVENTION

In one aspect, the present invention relates to methods for preparing bioactive polypeptides in an inactive form. In another aspect, the present invention relates to bioactive polypeptides such as neurotoxins, and to methods for the preparation of such neurotoxins. In yet another aspect, the invention relates to the use of inactivated neurotoxin compositions for the study and treatment of viral and neurological diseases.

BACKGROUND OF THE INVENTION

Bioactive polypeptides are typically obtained by either the recovery and purification of natural products, or by synthesis using its genetic counterpart. Typically, the polypeptides, whether purified from natural sources or synthesized using recombinant technology, are ultimately provided in a form having the intended bioactivity.

Occasionally, however, it is desirable to prepare otherwise bioactive polypeptides in their inactive form, in which they can be used for other in vivo purposes, such as the preparation of vaccines. In other situations, the bioactivity of the polypeptide itself may be a particularly toxic one, so as to make the recovery of the active polypeptide either unnecessary, or unduly difficult and dangerous.

Typically, even toxic polypeptides are first recovered in their native, active forms, and thereafter subjected to processes intended to either temper the bioactivity, or render the polypeptide completely inactive. Examples of such processes include heating the polypeptide (e.g., denaturation), oxidation (e.g., by peroxide, catalase treatment), and the like. Such processes, however, are typically non-specific in nature, generally irreversible, and potentially quite damaging to the polypeptide.

Certain proteins can be inactivated by the cleavage of disulfide linkages, for instance using a suitable reducing agent (e.g., 2-mercaptoethanol) to provide a corresponding pair of cysteine residues. Cleavage of disulfide linkages within a protein will typically result in the unfolding of the protein. Unless maintained in the cleaved and unfolded state (e.g., in the presence of urea), the disulfide bonds are often able to spontaneously reform, although not always pairing the same original residues (resulting in a malfolded product).

Ribonuclease, for instance, contains four disulfide bonds that can each be cleaved in the manner described above. Under appropriate conditions, the molecule can spontaneously reform in a manner that provides 95–100% of the original activity. On the other hand, if the three disulfide bonds of insulin are cleaved under similar conditions, the molecule will spontaneously reform to provide only 5–10% of the original activity. Hence, the linear amino acid sequence of a protein is not necessarily the sole determinant of the protein's folding pattern and activity.

The recovery of neurotoxins is a prime example of the difficulties involved in handling and using bioactive molecules. See, generally, "Cloning, Characterization, and Expression of Animal Toxin Genes for Vaccine Development", L. A. Smith, J. Toxicol.-Toxin Reviews, 9(2), 243–283 (1990). The Smith article describes, for instance, the related properties of a number of toxins from animal origin (p. 247), and the slow progress made to date in developing such vaccines.

The venom obtained from snakes such as those of the genus Naja has been found to contain a number of different physiologically active, and potentially useful, polypeptides having enzymatic and/or toxic effects. A number of these toxins have been purified and modified for the purpose of determining their molecular structure and mode of action.

In order to safely use such toxins, for instance, U.S. Pat. Nos. 3,888,977, 4,162,303 and 4,126,676 (each naming Sanders) disclose detoxified venom compositions. The compositions are detoxified by oxidation using catalase or peroxide, in a manner said to retain the neurotropic activity of the modified venom compositions. The Sanders patents discuss compositions derived from the venom of the Bungarus genus, the Naja genus and a combination of both genuses. Included in such patents are methods for determining the potency and atoxicity of such modified neurotoxins.

Neurotoxin polypeptides in their detoxified but neurotropically active form have been considered for the treatment of certain viral infections. Detoxified polypeptides have been considered, for instance, for use in the treatment of certain disorders such as the neurological disorder amyotrophic lateral sclerosis ("ALS"), a disease characterized by slow progressive degeneration of lower motor neurons. See, for instance, "The Use of Sanders Neurotoxoid I (Modified Snake Venom) in the Treatment of Recurrent Herpes Simplex of the Cornea: Progress Report", Clark, W. B., et al., *Southern Medical Journal* 55(9):947–951 (1962).

A variety of polypeptides, including toxins, have also been cloned and expressed by genetic engineering. See, for instance, the above-cited Smith article, which (beginning at page 257) describes a number of efforts directed at cloning snake venom toxin genes.

Conventional methods for preparing inactive polypeptides (e.g., detoxified neurotoxins) continue to suffer from a number of drawbacks. Among these drawbacks are the contaminants that frequently accompany the detoxified preparations. Another drawback relates to the fact that neurotoxins, unlike most polypeptides of a similar size, tend to be quite soluble in solvents commonly used for protein precipitation, thereby limiting the usefulness of conventional purification techniques. Yet another drawback relates to the use of any nonspecific means for rendering a polypeptide biologically inactive, since such means can often lead to the destruction of all properties of the molecule, including such desirable properties as immunogenicity and antiviral activity.

What is clearly needed is a method for the preparation of inactivated bioactive polypeptides, such as neurotoxins, in a manner that avoids the drawbacks associated with prior methods. To applicants knowledge, there have been no teachings in the art of the use of genetic engineering techniques, particularly in the manner provided herein, to prepare inactive forms of bioactive molecules such as neurotoxins.

SUMMARY OF THE INVENTION

In one aspect, the present invention provides a method of preparing a parenteral composition comprising an inactivated bioactive polypeptide, the method comprising the steps of:

a) identifying a polypeptide having a biological activity dependent on the presence of one or more disulfide bridges in its tertiary structure, b) preparing a CDNA strand encoding the polypeptide,
c) expressing the CDNA under conditions in which the polypeptide is recovered in an inactive form due to the failure to form one or more disulfide bridges, and
d) recovering the inactive polypeptide and formulating it into a composition suitable for parenteral administration to a host.

In a further aspect, the invention provides a method of administering a composition comprising an inactivated bioactive polypeptide to a host, comprising the step of providing the polypeptide in an inactive form and in a composition that facilitates its administration to the host. In a related aspect, the invention provides a host having administered such a composition.

In another aspect, the invention provides a composition comprising a bioactive polypeptide that has been rendered inactive by virtue of the failure to form one or more of its disulfide bridges. In a related aspect, the invention provides a composition for in vivo administration comprising a bioactive polypeptide that has been inactivated in the manner described herein.

The method can be used to prepare a variety of bioactive polypeptides, including "Group I neurotoxins" (namely, toxins affecting the presynaptic neurojunction), Group II neurotoxins (namely those affecting the postsynaptic neurojunction), and Group III neurotoxins (those affecting ion channels). cDNA sequences for such polypeptides are generally known, or can be determined using conventional techniques.

The cDNA can be expressed using any suitable expression system, under conditions in which the product can be recovered with one or more disulfide bridges unformed. Suitable expression systems include heterologous host systems such as bacteria, yeast or higher eucaryotic cell lines. Examples of useful systems are described, for instance, in "Foreign Gene Expression in Yeast: a Review", Romanos, et al., Yeast, 8:423–488 (1992). See also, "Yeast Systems for the Commercial Production of Heterologous Proteins", Buckholz, et al., Bio/Technology 9:1067–1072 (1991), the disclosures of both Romanos et al. and Buckholz et al. being incorporated herein by reference.

These articles are generally directed at the more common goal of affirmatively achieving posttranslational processing and extracellular secretion. Under such conditions, the formation of appropriate disulfide linkages would be included as a necessary step. Given the present description, however, these articles, and the techniques described therein, will be of considerable use to those skilled in the art in achieving the recovery of the unfolded product, e.g., by intracellular expression in yeast.

Preferably, the cDNA is expressed using a yeast expression system, such as *Saccharomyces cerevisiae* and *Pichia pastoris*. More preferably, the cDNA is expressed in a Pichia expression system under conditions in which the product is cytoplasmically produced, as opposed to extracellularly secreted. In an exemplary embodiment, the polypeptide is expressed using a Pichia expression system, under conditions in which the leader sequence of naturally-occurring cDNA is removed and replaced with only the initiation codon.

Polypeptides of the present invention are generally stable under suitable conditions of storage and use in which the disulfide bonds are prevented from spontaneously reforming, or are allowed to reform in a manner that precludes the undesirable activity of the polypeptide. Optionally, and preferably, once the inactive polypeptide has been recovered, it is treated by suitable means to ensure that the cysteine residues do not spontaneously reform to form disulfide bridges. An example of a preferred treatment means is the use of ozone treatment as described herein. Alternatively, as will be described in greater detail below, ozone treatment can itself be used to selectively break (i.e., oxidize) the disulfide bonds of a native or recombinantly prepared toxin molecule in order provide a stable, inactive form thereof.

In another optional, and alternative, embodiment a polypeptide such as neurotoxin is produced in an inactive form using the Pichia expression system described herein. To the best of Applicants knowledge, the prior art fails to teach or suggest the preparation of a toxin in inactive form by the route of cytoplasmic expression in yeast.

The method and composition of the present invention provide a unique and valuable tool for the synthesis and recovery of bioactive polypeptides in a manner capable of diminishing undesirable activity, yet retaining other useful properties of the polypeptide (such as immunogenicity and antiviral activity).

DETAILED DESCRIPTION

As used herein, the following words (and inflections thereof) and terms will have the meanings ascribed to them below:

"bioactive" will refer to a polypeptide capable of eliciting at least one biological response when administered in vivo.

"polypeptide" will refer to any biomolecule that is made up, at least in part, of a chain of amino acid residues linked by peptide bonds.

"inactive" will refer to a polypeptide that is provided in a form in which at least one form of its bioactive responses is substantially terminated or decreased to a desired extent.

"neurotoxin" will refer to a bioactive polypeptide wherein at least one activity (e.g., binding to the acetylcholine receptor) produces a toxic effect on the nervous system of a mammalian host.

The method of the present invention involves an initial step of identifying a bioactive polypeptide having a tertiary structure in which bioactivity is dependent, at least in part, on the formation of one or more disulfide bridges between cysteine residues. Typically, the polypeptide will be one that is naturally secreted in the course of its synthesis, since it is the secretion process that will provide the necessary post-translational steps, including disulfide bond formation. Preferably, the polypeptide is one that is stable when recovered and that retains other desirable properties in the unfolded state, such as immunogenicity and/or antiviral, anti-tumor or wound healing activity.

The amino acid sequence and tertiary structure of a number of bioactive polypeptides is known. Suitable polypeptides include those in which one or more disulfide bridges are known to form in the natural configuration, and in which such bridge(s) are necessary for the bioactivity of the polypeptide. Such bridges can be of either an intramolecular (i.e., within a single polypeptide) nature and/or an intermolecular (e.g., between discrete subunits) nature.

Secreted or cell-surface proteins often form additional covalent intrachain bonds. For example, the formation of disulfide bonds between the two —SH groups of neighboring cysteine residues in a folded polypeptide chain often serves to stabilize the three-dimensional structure of the extracellular proteins. Protein hormones such as oxytocin, arginine vasopressin, insulin, growth hormone and calcitonin, all contain disulfide bonds. Enzymes such as ribonuclease, lysozyme, chymotrypsin, trypsin, elastase and papain also have their tertiary structure stabilized by disulfide bonds. Besides the bioactive proteins listed above, there are numerous other proteins that contain disulfide bonds, such as the immunoglobulins (IgA, IgD, IgE, IgM), fibronectin, MHC (major histocompatible complex) molecules and procollagen. Many polypetides from animal venoms also contain disulfide bonds.

In a preferred embodiment, the method of the present invention is used to prepare inactivated forms of neurotoxins, and more preferably neurotoxins from amongst the four groups provided below. As described above, those in Group I typically affect the presynaptic neurojunction, those in Group II typically affect the postsynaptic neurojunction, and those in Group III typically affect ion channels. Lastly, there are also included toxins known only to have a toxic affect by causing membrane damage.

| | Neurotoxins | | Membrane-damaging |
|---|---|---|---|
| Group I | Group II | Group III | toxins |
| notexin | α-conotoxin | dendrotoxins | myotoxins |
| β-bungarotoxin | α-cobrotoxin | scorpion toxins | cardiotoxins |
| crotoxin | erabutoxin | μ-conotoxins | mellitin |
| taipoxin | α-cobratoxin | sea anemone | phospholipases |
| textilotoxin | α-bungarotoxin | toxins | |
| α-latrotoxin | | | |

The method involves a further step of preparing or isolating a corresponding gene (e.g., a cDNA strand) encoding the polypeptide. Using the primary amino acid sequence discussed above, and in view of the present teaching, those skilled in the art will appreciate the manner in which such polypeptides can be synthesized using genetic engineering techniques. Generally, and preferably, one or more of the native control (e.g., leader) sequences of the desired cDNA are removed and replaced with one or more corresponding sequences in order to facilitate the desired expression.

Polypeptide components from animal venoms, for instance, can be obtained from the animals themselves or from other sources, or they can be created in the laboratory using conventional protein engineering techniques. In the former approach, animals are induced by mechanical or electrical stimuli to release venom from their glands, which travels through a venom canal and out the fang or stinger. The venom is collected and various constituents of the venom are purified by conventional chromatographic techniques.

In the latter approach, constituents from the venom are synthesized by cloning the genes encoding the various polypeptide elements and expressing these genes in heterologous host systems such as bacteria, yeast or higher eucaryotic cell lines. Yeast expression systems are presently preferred, since they tend to provide an optimal combination of such properties as yield and adaptability to human use products.

Expressed products are then purified from any other contaminating host polypeptides by means of chromatographic techniques similar to those used to isolate the polypeptides directly from the venom.

There are significant advantages to the use of host systems other than the venomous animals to obtain the venom components. The danger to human lives in obtaining the venom from the animal is eliminated. There will no longer be a need for the costly animal husbandry required to maintain venomous animals for venom extraction. The quantities of materials that can be obtained from the genetic engineering approach can be one or more orders of magnitude greater than the quantities that can be derived from the venom itself. Moreover, once the gene(s) is cloned and expressed, it can be used to provide a continual, reproducible source in the form of a bacterial, yeast or higher eucaryotic cell line seed culture.

Seed cultures can be stored and transported in the frozen state, lyophilized, or, in some cases, plated on media. Also, the use of genetic engineering tools will enable those skilled in the art to manipulate the genes for the purpose of altering the polypeptide product in any fashion feasible. Using the method of the present invention, in combination with available tools for protein engineering (e.g., site-directed mutagenesis), those skilled will be able to prepare a bioactive polypeptide having any desired level of toxicity, whether non-toxic, or of diminished, equal or greater toxicity than the native form.

The method of the invention provides a further step of expressing the cDNA under conditions in which the polypeptide is recovered in an inactive form due to the failure to form one or more disulfide bridges. As described in greater detail below, this step involves the avoidance of posttranslational processes that would otherwise serve to form such linkages.

Optionally, and preferably, the method provides a further step of treating the inactivated bioactive polypeptides in order to retain the cysteine residues and prevent the spontaneous formation of disulfide bonds. A preferred treatment includes ozone treatment, in the manner described herein. Ozonation affects the cysteine residues by converting the pendent sulfhydryl (—SH) groups to corresponding —SO3X groups, which, unlike the sulfhydryl groups, are unable to form a disulfide bridge. Such treatment is not necessary, however, for those inactivate polypeptides that are found to not spontaneously reform, and that provide the desired activity. Ozonation is preferred for polypeptides such as neurotoxins, where Applicant has shown that upon cleavage and ozonation of the sulfhydryl groups, native neurotoxins are both stable and active.

The invention further provides a bioactive polypeptide that has been rendered inactive by virtue of the failure to form one or more disulfide bridges. Such polypeptides can be stably stored and used under conditions in which disulfide bonds are prevented from spontaneously reforming.

In yet another aspect, the invention provides a method of administering a bioactive polypeptide to a host, comprising the step of providing the polypeptide in an inactive form and within a suitable composition, and administering the composition to a host. In a related aspect, the invention provides a host having administered such a polypeptide. Compositions of the present invention can be used for a variety of purposes. Compositions are particularly useful in situations calling for a polypeptide in a form that is as close to native as possible, yet without an unwanted bioactivity.

The invention may be more easily appreciated by reference to the following non-limiting examples in which parts are expressed by weight unless otherwise indicated. The disclosures of each of the references cited herein are incorporated by reference.

EXAMPLES

Example 1

Isolation of Gland Tissue for RNA Extraction

The following protocol was used to clone the gene encoding α-cobratoxin from the venom of *Naja naja siamensis*.

(a) Recovery of Venom

*Naja naja siamensis* snakes were obtained from Siam Farms, Bangkok, Thailand. Animals were shipped to and housed at Ventoxin, Inc., Frederick, Md. USA. The venom glands from *N. n. siamensis* animals were surgically removed and used to prepare mRNA for generating a cDNA library. Snakes were placed on a schedule for milking (venom extraction). They were milked on day 1 and eight days later milked a second time. On the 2nd or 3rd day, they were anesthetized with sodium pentobarbital and their glands removed (Vandenplas et al., 1985). Gland tissue was quickly cut into small pieces and immediately frozen in liquid nitrogen. Samples were kept at −70° C. until use.

(b) RNA Isolation

Total RNA was isolated from gland tissue by using a standard guanidinium/hot phenol method (Feramisco et al., 1982). Frozen gland tissues (5 g) were placed in a polytron mixer and 10 ml of Solution A (guanidinium isothiocyanate mixture) was added to the tissue. Solution A was prepared by resuspending 100 g of guanidinium isothiocyanate in 100 ml of deionized water, 10.6 ml of 1 M Tris-Cl (pH 7.6), and 10.6 ml of 0.2 M disodium ethylene diamine tetraacetate (EDTA). It was stirred overnight at room temperature.

The solution was then warmed while stirring to 60–70° C. for 10 min to assist dissolution. Any insoluble material remaining was removed by centrifugation at 3000 g for 10 min at 20° C. To the guanidinium isothiocyanate solution, was added 21.2 ml of 20% sodium lauryl sarkosinate and 2.1 ml of β-mercaptoethanol to the supernatant and the volume was brought to 212 ml with water. The final solution was filtered through a disposable Nalgene filter and stored at 4° C. in a tightly sealed, brown glass bottle.

The glands were mixed in the polytron mixer at 4° C. until most of the tissue had been disrupted (about 3–5 min.). The gland solution was placed in a 50 ml polypropylene centrifuge tube and 20 ml more of the guanidinium isothiocyanate mixture was added. The mixture was brought to 60° C. and passed through a syringe fitted with an 18 gauge needle. This shearing technique was repeated 2 to 3 times or until the viscosity of the suspension was reduced. An equal volume of ultra pure liquid phenol preheated to 60° C. was added to the tissue suspension and this was again passed through the syringe 2 to 3 times.

At this point, 0.5 volume of Solution B (0.1 M sodium acetate (pH 5.2), 0.01 M Tris-Cl (pH 7.4), 0.001 M. EDTA) was added to the emulsion and mixed. An equal volume of chloroform/isoamyl alcohol (24/1 v/v) was added and the mixture shaken vigorously for 15 min. while maintaining the temperature at 60° C. The mixture was cooled on ice and centrifuged at 2000 g for 15 min. at 4° C. The aqueous phase, containing the RNA, was recovered and reextracted with phenol/chloroform. To the aqueous phase was added 2 volumes of absolute ethanol and the mixture was stored at −20° C. overnight. All glassware used in extracting and working with RNA had been baked at 250° C. for at least 4 h. Sterile, disposable polypropylene plasticware is essentially free of RNase and can be used for the preparation and storage of RNA without pretreatment.

The RNA was recovered by centrifugation was dissolved in 30 ml of Solution C (0.1 M Tris-Cl, pH 7.4, 0.05 M NaCl, 0.01 M EDTA, 0.2% (v/v) sodium dodecyl sulfate (SDS)). Proteinase K was added to a final concentration of 200 ug/ml and incubated at 37° C. for 2 h. The solution was then heated to 60° C. and 0.5 volume of phenol, preheated to 60° C., was added and mixed vigorously with the RNA-containing solution. Chloroform (0.5 volume) was added to the solution and again mixed vigorously at 60° C. for 10 min. The solution was cooled on ice for 10 min. and then centrifuged at 2000 g for 15 min.

The aqueous phase was recovered and re-extracted one more time with phenol/chloroform at 60° C. The aqueous phase was recovered and reextracted twice with chloroform at room temperature. To the aqueous phase was added 2 volumes of absolute ethanol and put at −20° C. overnight. The nucleic acids were precipitated by centrifugation and the pellet rinsed with 70% cold ethanol. RNA was stored at −70° C. in 70% ethanol until used. When the RNA was ready to be used, it was centrifuged, dried and resuspended in Rnase-free sterile water.

(c) mRNA Purification

Poly(A)+RNA was enriched by passage over an oligo (dT)-cellulose column using a conventional method (Aviv and Leder, 1972). Commercial oligo(dT)-cellulose was equilibrated with sterile, RNase-free Solution D (0.02 M Tris-Cl, pH 7.6, 0.5 M NaCl. 0.001 M EDTA and 0.1% (v/v) SDS). A 1.0-ml bed-volume of equilibrated matrix was poured into either an Rnase-free disposable polypropylene column or siliconized RNase-free pasteur pipette. The matrix was washed with 3 column volumes of (1) Rnase-free sterile water; (2) 0.1 M NaOH containing 0.005 M EDTA; and (3) sterile water. The column effluent should have a pH less than 8. The column was then washed with 5 volumes of sterile Solution D.

The RNA isolated as described above was heated to 65° C. for 5 min and a 2× concentration of an equal volume of Solution D was added to the RNA solution. The sample was cooled to room temperature and loaded onto the oligo(dT)-cellulose column. The flow-through from the column was heated to 65° C., cooled to room temperature, and reapplied to the column. The column was washed with 10 volumes of Solution D followed by 4 column-volumes of Solution D containing 0.1 M NaCl. The poly(A)+RNA was then eluted with 2–3 column volumes of sterile Solution E (0.01 M Tris-Cl, pH 7.5, 0.001M EDTA and 0.05% (v/v SDS).

Typically, NaCl was added to the mRNA to obtain a salt concentration of 0.5 M, and the mRNA was repurified on a second passage over the oligo(dT)-cellulose column using the same procedures as described for the initial column run. Sodium acetate (NaOAc) (3M, pH 5.2) was then added to the mRNA from the second column run to obtain a final concentration of 0.3 M NaOAc. Cold absolute ethanol (2.5 volumes) was added to the mRNA solution and the solution was placed at −20° C. overnight. The *N. n. siamensis* mRNA was then centrifuged at 12,000 g, the pellet washed with cold 70% ethanol, and stored in 70% ethanol at −70° C. until used. The yield of mRNA from 5 g of gland tissue was 16 μg.

(d) Construction of a *N. n. siamensis* cDNA Library.

Complementary DNA (cDNA) was prepared from 5 μg of *N. n siamensis* mRNA (Guber and Hoffman, 1983) using commercially-available cDNA synthesis kits. A variety of sources provide cDNA synthesis kits that are useful for such purposes. In this particular case, cDNA synthesis kit, EcoR I/Not I adaptors, T7 sequencing kit, Deaza T7 sequencing mixes, and restriction enzymes were obtained from Pharmacia (Piscataway, N.J.).

A lambda ZAP II/EcoR I CIAP treated vector kit and Gigapack II Gold packaging extract were obtained (Stratagene, LaJolla, Calif.), as was a "GeneAmp PCR reagent kit" (Perkin-Elmer Cetus, Norwalk, Conn.). Oligonucleotides used for screening cDNA libraries and as primers for polymerase chain reactions (PCR) and dideoxynucleotide sequencing were synthesized on a Biosearch 8700 DNA synthesizer by β-cyanoethyl phosphoramidite chemistry and purified on Oligo-Pak columns (MilliGen/Biosearch, Burlington, Mass.).

A protocol for the cDNA synthesis is provided in "You-Prime cDNA Synthesis Kit Instructions", Pharmacia LKB Biotechnology, the disclosure of which is incorporated herein by reference. (See, in particular, pages 12, 13, 18, 19 and 29 and Procedures A, B and D thereof for the prototypical procedure.) Using procedure B, hemiphosphorylated adaptors containing Not I and EcoR I restriction enzyme sites were ligated to the termini of the synthesized, double-stranded cDNA prepared in Procedure A. After purification of the cDNAs (Procedure D), the N. n. siamensis cDNA were inserted into EcoR I-predigested, phosphatased Lambda ZAP II arms and packaged into viable phage particles by using packaging extracts. The latter was accomplished using a commercially available kit from Stratagene (LaJolla, Calif.) (Catalog #236211, "Predigested Lambda ZAP II/EcoR1 Cloning Kit").

N. n. siamensis cDNA was ligated to Lambda ZAP II arms using the procedure on page 3 of the Strategene instructions (substituting the test insert for the N.n. siamensis cDNA). The ligated sample was then packaged into viable phage particles using a "Gigapack Gold" packaging extract from Strategene (product insert, page 4). The recombinant bacteriophage was used to infect E. coli host strain, XL1-Blue, which generated the primary cDNA library. The primary library contained approximately $1.35 \times 10^5$ pfu/µg mRNA.

(e) Isolation of α-cobratoxin cDNA from the cDNA Library and Subcloning of cDNA Inserts from Lambda ZAP II Clones Approximately 100,000 plaques from an amplified cDNA library were analyzed for sequences encoding α-cobratoxin using a degenerate oligonucleotide probe prepared from the known amino acid sequences of α-cobratoxin. The probe (LAS 1) was prepared as follows:

5'-GGNCANGTNT GYTAYACNAA RACNTGGTGY GANGCNTTNT G (Referred to herein as SEQ ID NO: 1; wherein "N" represents the nucleoside inosine wherever it appears in the sequence, Y represents a nucleotide which may be either thymine or cytosine, and R represents a nucleotide which may be either adenine or guanine)-3'

The oligonucleotide probe above was end-labelled on the 5' end using [$^{32}$P]-γ-ATP and T4 polynucleotide kinase using standard protocols (Sambrook et al. 1989). The library was screened for the presence of α-cobratoxin cDNA on nitrocellulose filters according to standard procedures (Sambrook et al., 1989). Filters were prehybridized for 4 h at 42° C. in 6×SSC (90 mM sodium citrate containing 0.9 M NaCl, pH 7.0), containing 1×Denhardt's and 100 mg/ml sonicated and denatured salmon sperm DNA. Filters were then hybridized in 4×SSC, pH 7.0, containing 1×Denhardt solution (50×=5 g ficoll, 5 g polyvinylpyrrolidone, 5 g bovine serum albumin/500 ml water) and the radiolabelled oligonucleotide probe for 16 h at 42° C.

Successive washes were performed in 2×SSC, pH 7.0, at 37° C. for 30 min before autoradiography for 16 h at –70° C. using X-AR film with intensifying screens. Double-stranded cDNA inserted into the multiple cloning site (MCS) of pBluescript SK-contained within lambda ZAP II, were removed as phagemids by an in vivo excision process designed by Stratagene (LaJolla, Calif.) (see Stratagen insert, page 7, "In Vivo Excision Protocol"). Colonies from the in vivo excision were selected by ampicillin resistance, propagated, and the phagemids were isolated by alkaline extraction (see pp. 368–369, "Analysis Lysis Method"). The size of the inserts from the recombinant phagemnids were measured on agarose gel electrophoresis after digestion with the restriction enzyme, EcoR I.

(f) Characterization of the α-Cobration cDNA by Asymmetric PCR and DNA Sequencing The template for asymmetric PCR was double-stranded pBluescript SK-containing cDNA inserts of approximately 400 bp. Oligonucleotides designated as LAS 2 (5' GAGTTAGCTC ACTCATTAGG C (Referred to herein as SEQ ID NO:2) 3') and LAS 3 (5' ATTTTCATTC GCCATTCAGG C (Referred to herein as SEQ ID NO:3) 3') were used as primers in asymmetric PCR (see "T7 Sequencing Kit Instructions", Pharmacia LKB Biotechnology"). Sanger dideoxynucleotide sequencing employed T7 DNA polymerase according to the manufacturer's protocol accompanying the T7 Sequencing (TM) Kit of Pharmacia LKB Biotechnology. N. n siamensis cDNA template, and the primers (LAS 4 and LAS 5) were as described below. Single stranded DNA was used as a template. Programs for sequence analysis from Intelligenetics,Inc. (Mountain View, Calif.), including GENED, SEQ, and IFIND, were used on a VAX from Digital Equipment Corp. (Maynard, Mass.). One of the cDNAs sequences encoded α-cobratoxin (identified as Naja naja kaouthia cDNA library clone "NNK III 6.2"). The α-cobratoxin cDNA was an incomplete gene in that the leader sequence coding for the snake signal sequence was incomplete (–1 to –20) lacking an in initiation codon (ATG). For purposes of expression, this was immaterial, since the leader sequence was replaced with a functional start codon and restriction enzyme site (as described herein with reference to expression of cDNA in yeast).

The gene encoding α-cobratoxin could also have been prepared using the genetic coding sequence for the known amino acid sequence of the protein, and synthetically constructing a suitable gene using automated biochemical techniques.

The PCR-derived DNA was resuspended in TE buffer (20 mM tris-CL, 1 mM EDTA, pH 7.5) and cleaved with the restriction enzyme, EcoR I (see Gibco product insert for EcoR I catalog #15202-013, restriction enzyme assay for EcoR I). The yeast DNA vector (pHILD4) was also taken, resuspended in TE buffer and cleaved with EcoR I.

The vector DNA was cleaved in the same manner as the PCR-derived DNA (see Gibco instructions). After digestion with EcoR I, the PCR-derived DNA and yeast vector DNA was purified by the addition of an equal volume of phenol/chloroform (50/50 v/v), vortexing, and centrifugation in a microfuge (12,000 g). A second chloroform extraction was performed (equal volume of CHCl$_3$ and sample), vortexing, centrifugation and ethanol precipitation. Ethanol precipitation was performed by adding sodium chloride to the sample (0.2 M final concentration) and 2.5 volumes of cold ethanol. After mixing, the sample was placed on dry ice for 15 min, then centrifuged at 4° C. in a microfuge (12,000 g) for 15 min. The DNA pellet was dried under vacuum.

Both of the EcoR I-treated DNAs were resuspended in TE buffer and covalently joined together using T4 DNA Ligase (see insert materials, Gibco BRL, Cat. # 5224SC, T4 DNA Ligase). The ligated DNA was used to transform competent E. coli cells (see Enclosure 10 for transformation conditions). Transformants growing on TB agar (Terrific Broth+agar) containing ampicillin (100 µg/ml) were isolated and the recombinant DNA analyzed by restriction enzyme analysis.

Optionally, the DNA can be purified from E. coli cells, e.g., in the manner described in "Wizards Maxipreps DNA Purification System", Promega. Recombinant DNA from clones harboring the α-cobratoxin gene/pHILD4 construct was used for integration into the yeast, Pichia pastoris.

(g) Cloning and Cytoplasmic Expression

Expression of the α-cobratoxin gene in the vector, pHILD4 yields a cytoplasmic product that lacks posttranslational modifications, including disulfide bond formation.

Suitable techniques for cloning and expressing genes into *Pichia pastoris* have been developed by the Phillips Petroleum Company and compiled in "Pichia Expression Kit—A Manual of Methods for Expression of Recombinant Proteins in *Pichia pastoris*", which was prepared by Invitrogen and accompanies their expression kit having catalog # K1710-01.

The gene encoding α-cobratoxin from amino acids +1 to +71 can be removed from the cDNA by using the following polymerase chain reaction primers:

(a) 5' sense primer (LAS 4)=5'-GGATCCGAAT TCACG ATG ATA AGA TGC TTC ATA ACA (Referred to herein as SEQ ID NO:4)-3' (36 mer) and (b) 3' antisense primer (LAS 5)=5'-CCTAGGGAAT TCT-TATCA AGG ACG TTT GCG TGT TGG (Referred to herein as SEQ ID NO:5)-3' (36-mer).

Recombinant DNA prepared as described herein was treated with Sst I restriction enzyme under the same reaction conditions as described above with respect to EcoR I, except using reaction buffer No. 2 described in the above-captioned Gibco EcoR I product insert. The restricted DNA is purified by the addition of an equal volume of phenol/chloroform (50/50 v/v), vortexing, and centrifugation in a microfuge (12,000 g).

A second chloroform extraction was performed (equal volume of $CHCl_3$ and sample), vortexing, centrifugation and ethanol precipitation. Ethanol precipitation was performed by adding sodium chloride to the sample (0.2 M final concentration) and 2.5 volumes of cold ethanol. After mixing, the sample was placed on dry ice for 15 min, then centrifuged at 4° C. in a microfuge (12,000 g) for 15 min. The DNA pellet was dried under vacuum and resuspended in TE buffer.

The DNA pellet is then integrated into the chromosome of *Pichia pastoris* strain GS115 using conventional procedures for integrating genes into *Pichia pastoris* (e.g., p. 29–38, "Growth of Pichia for Spheroplasting") and expressing the integrated genes (pp. 41–45, "Expression of Recombinant Pichia strains").

Example 2

Recovery and Yield

A fermentation of a cytoplasmically-expressing clone harboring the gene encoding α-cobratoxin can be performed in a 5 L New Brunswick BioFlo III fermentor. The size of the fermentation can be scaled up or down depending on the requirement for product. For a 5 L batch, a frozen seed culture containing the α-cobratoxin construct is used to inoculate 10 ml of MGY media (see attached media recipe) in a test tube. After 18 to 20 hours growth at 30° C., 0.5 ml is used to inoculate 50 ml of MGY in a 250 ml flask. After 36 to 38 hours of growth, the entire 50 ml is used to inoculate the 5 L fermentor. The fermentation is performed in a basal salt medium with 26.7 ml 85% phosphoric acid, 0.93 g/L calcium sulfate-$2H_2O$, 18.2 g/L potassium sulfate, 14.9 g/L magnesium sulfate, 4.13 g/L potassium hydroxide, 40 g/L glycerol and 2 m/L of basal salts (PTM) are added. PTM basal salts consist of 2.0 g cupric sulfate, 0.08 g sodium iodide, 3.0 g magnesium sulfate, 0.2 g sodium molybdate, 0.02 g boric acid, 0.5 g cobalt chloride, 7.0 g zinc chloride, 22 g ferrous sulfate, 0.2 g biotin and 1 ml sulfuric acid per liter. The fermentation culture is fed with a 50% solution of glycerol in deionized water, while the methanol feed solution is 100% methanol with 2 ml of PTM basal salts and 1 mg biotin per liter. "Structol" brand antifoamer can be used as antifoam control; the pH during the glycerol phase is maintained at pH 5.0 using 30% ammonium hydroxide; dissolved oxygen is controlled above 25% saturation by supplementing with pure oxygen.

A standard fermentation procedure is followed which includes an initial batch phase followed by a 4 hour glycerol fed-batch with a feed rate of 15 ml/L/h of a 50% glycerol solution. At the completion of the glycerol fed-batch phase the methanol induction phase is started. The rate of methanol feeding is increased gradually from 3.5 to 12 ml/L/h within 6 to 8 hours and maintained at 12 ml/L/h. Samples are taken during fermentation for measuring optical density at $600_{nm}$, cell dry weight and SDS-PAGE analysis.

Yeast cells are recovered from the fermentation by centrifugation. Cells are washed in breaking buffer (50 mM $NaH_2PO_4$, 1 mM EDTA, 5% glycerol, 1% PMSF, pH 6.0), and resuspended in the same buffer prior to disruption in an APV Matnon Gaulin 30CD pilot scale homogenizer. Cell debris is removed by centrifugation and a PEI precipitation is performed on the cell extract in order to remove endogenous nucleic acids. Polyethyleneimine (PEI) (10%) is added to the cell extract to obtain a final concentration of 0.4% PEI. The mixture is allowed to sit for 3 to 5 hours at 4° C. with stirring. The mixture is centrifuged at 27,000×g for 15 min and the supernatant is dialyzed against 50 mM $NaH_2PO_4$, pH 6.0 at 4° C. The recombinant product is purified by ion exchange (eg., cationic exchange matrix) and molecular sieve chromatography.

There have been a number of heterologous proteins produced using the *Pichia pastoris* expression system. The levels of expression from intracellularly expressed proteins has ranged from 0.3 to 12 g/L depending on the protein expressed (*Biotechnology* 11, 905–910 (1993)). The level of expression is usually dependent on such factors as the genetic construct itself, cell copy number and fermentation optimization (eg., cell density, optimal pH and dissolved oxygen concentration). Yields from an α-cobratoxin gene expressed intracellularly in *Pichia pastoris* will typically fall in the range stated above.

Example 3

Ozonation

Ozone ($O_3$), a powerful oxidant, is used for water disinfection. In the course of the present invention, ozone treatment is preferably used to treat the recovered, inactive polypeptide in order to render it incapable of spontaneous reformation. Optionally, ozonated pure water can be used to itself selectively break the disulfide bonds of a formed polypeptide in order to provide an inactive, denatured, and stable form thereof.

Ozone treatment can be used to quickly provide microbial sterilization and disinfection, organic compound destruction, and conversion of iron or manganese salts to insoluble oxides which can be precipitated from the water. The major reaction byproducts are water, oxygen and carbon dioxide. For environmental and safety concerns, unreacted or residual ozone should be monitored. A number of UV spectrophotometric methods can be used to determine the level of ozone in water or physiological saline. Ozone has an absorption peak at 260 nm whereas oxygen does not absorb at this wavelength. When ozone concentration was measured in ice water (1° C.±1° C.) by three different colorimetric methods, the absorbance coefficient in ozone at 260 nm as $A_{1cm}^{1mg/L}$ is 0.11.

A wavelength scan of ozonated water was determined at various dilutions. Using the same ozonated water, the ozone concentration was determined by Accuvac method described below. Using this, or similar methods, it is possible to calculate the ozone content of the ozonated water in mg of $O_3$/L.

A standard curve for the ozonated water was also prepared. From this curve one can derive the absorbance coefficient of ozone in any given solution. Table 1 below provides a representative relationship between absorbance coefficients and concentration for ozonated water. Absorbance coefficient $(A)^{mg/l}$=(Absorbance at 260 nm)÷(Concentration of Ozone)

TABLE 1

| Absorbance of Ozonated water at 260 nm | Concentration of Ozone by Accuvac method mg/L | Absorbance Coefficient of Ozone at 260 nm |
|---|---|---|
| 1.5717 | 13.48 | 0.11659 |
| 0.628 | 6.44 | 0.0975 |
| .39822 | 2.908 | 0.1369 |
| .25953 | 2.6792 | 0.0968 |
| .19797 | 1.722 | 0.11496 |
| .13605 | 1.28 | 0.1062 |
| AVERAGE VALUE | | 0.11 |

Three different colorimetric methods ("Accuvac", "Alizarin" and "Indigo Trisulphonate" methods) were used for the determination of ozone concentration in ice water (1° C.±1° C.), and compared to absorbance at 260 nm. Ozonated water was prepared as described in above. Certain of these methods are used by the International Ozone Association Standardization Committee.

METHOD 1: ALIZARIN METHOD

The method is directly applicable in the range of 0.03 to 0.6 mg/L. A stock solution of Alizarin violet 3R is made up as a 0.2 mM solution. Disperse 124.45 mg of the dye into an aliquot of distilled water in a 1 liter volumetric flask. Mix magnetically overnight. Add 20 mg of analytical grade sodium hexametaphosphate, 48.5 g of analytical grade ammonium chloride and 1.6 g of ammonia expressed as $NH_3$. Dilute with distilled water to 1 liter and stir overnight. A 10-fold dilution of this solution has an absorbance of 0.155 cm$^{-1}$) 20 ml of the reagent solution is introduced into each of two 200 ml volumetric flasks. Fill one flask with ozone free water. Fill the other flask with the sample water by introducing the sample below the surface of the dye solution to prevent ozone loss by degassing. When measured, the difference in absorbance at 548 nM is 2810 L/M/cm. This equates to the expression:

mg/L $O_3$ = Total volume(200 ml) × (change in absorption) ÷

(Cell length (1 cm) × 0.059 × volume of sampled water (180 ml))

METHOD 2: INDIGO TRISULPHONATE METHOD

The method is directly applicable in the range of 0.01 to 0.1 mg/L of ozone in water. A stock solution of indigo-trisulphonate is made up as a 1 mM solution by dispersing the dye into a solution of analytical grade phosphoric acid at a concentration of 1×10$^{-3}$ M. A 100-fold dilution of this solution has an absorbance of 0.16+/−0.01/cm at 600 nm and should be discarded if the absorbance is lower than 80% of the starting value. Normal stability lasts one month. As a diluted reagent, 20 ml of the stock solution is diluted to 1 liter together with 10 g of analytical grade $NaH_2PO_4$ and 7 ml concentrated analytical grade $H_3PO_4$ (stability of the diluted solution: one week).

In use, 10 ml of diluted reagent solution is introduced into each of two 100 ml volumetric flasks. Fill one flask with ozone free water (e.g. distilled water). Fill the other flask with the sample water by introducing the sample below the surface of the dye solution to prevent ozone loss by degassing. Measure the difference in absorbance at 600 nm between blank and sample with 5 or 10 cm cells. The measurement is to be made as soon as possible but preferably within 4 hours. The pH value of the measured solution must be lower than 4.

The proportionality constant is 0.42+/−0.01 /cm/mg/L ozone, which is equal to a difference in absorbance of 20 L/M/cm (Stoichiometry is considered as 1:1). mg/L ($O_3$)= (total volume (100 Ml)×Change in absorption)÷(cell length (cm)×0.42×Volume of sampled water (90 ml))

METHOD 3: ACCUVAC METHOD

As ozone reacts quantitatively with indigo trisulfonate (Blue indigo dye), the color of the solution fades. Color intensity is inversely proportional to the amount of ozone present, is then measured at 600 nm with a spectrophotometer. The reagent is formulated to prevent interference from any chlorine residual which may be present. The method is directly applicable in the range of 0 to 0.25 mg/L.

In use, gently collect at least 40 ml of sample in a 50 ml beaker. Collect at least 40 ml of ozone free water (Blank) in another beaker. Fill one Indigo ozone reagent Accuvac ampule with the sample and one ampule with the blank. This is done by immersing the ampule in the beaker which has the sample. Quickly invert the ampules several times to mix. Take an aliquot of the samples and read at 600 nm in spectrophotometer.

Read a blank value as X at 600 nm. 0.125 mg/L $O_3$ should have absorbance of x/2 g/L of $O_3$=(0.125×O.D. of the blank value/2)÷(O.D. of the sample at 600 nm×Dilution factor)

TABLE 2

| METHOD | OZONE CONCENTRATION (mg/L of water) | NOTE |
|---|---|---|
| Accuvac | 13.676 | |
| Alizarin | 16.8 | |
| Indigo - Trisulphonate | 15.85 | |
| UV absorption at 260 nm | 15.45 | (Abs/$A^{1\ cm/mg/1}$) 1.710/.11 |

Table 2 shows the ozone concentration, as determined by these various methods, for aliquots of the same ozonated water. From the results in TABLE 2 it can be seen that each method provides substantially the same concentration of ozone. Since all the four methods seem to be comparable to each other, the UV absorption method is preferred since it is simple and inexpensive to perform.

Ozone was produced by a high voltage discharge using Tri Atomic Oxygen Generator (Model No. 3, Serial No. 34 from modern Medical Technology Boca Raton, Fla.) The oxygen was passed through the generator to produce the ozone. Approximately 0.2% of ozone was produced in the equipment at the rate of bubbling used (about 200 ml/min). However, for quantitation studies a sample was taken with each series of experiments.

Absorption measurements were made in the Beckman DU 650 Spectrometer using cm quartz cuvettes. A standard curve was obtained by serially diluting the ozonated water and measuring the absorbance at 260 nm. The standard curve was also obtained by using a calorimetric method using commercially available Accuvac ampules (From Hach, P.O. Box 389, Loveland, Colo. 80539)

Saturated ozone water was prepared in the following manner. Oxygen was bubbled at the rate of 200 ml/min to ice water (1° C.±1° C.). The container with distilled water was kept in an ice bath during the ozonation. Ozone, bubbled into water or saline, was determined by measuring the absorbance at 260 nm. Using a 50 mL sample, it takes a minimum of 30 minutes to reach an absorbance reading of 2.0, although the time is dependent upon the oxygen input.

Since water that is saturated with oxygen will not become saturated with ozone, the flow rate of input oxygen was ideally kept at equal to or less than 260 mL/min. Once the ozonated water reaches an absorbance of 1.0 to 2.0, serial dilutions of the ice cold ozonated water were made and measurements of the absorbance at 260 nm were made. The ozonated water was also used to measure kinetics, and in particular, decay rate over the time. The serially diluted water was used to measure the ozone concentration by Accuvac method.

Water ozonated in this manner can be used to oxidize a formed polypeptide, in order to cleave the disulfide groups and render the polypeptide inactive. Alternatively, and preferably, the ozonate water can be used to stabilize a polypeptide that is prepared in an inactive form by the genetic engineering method described above. In either case, the oxidized peptide can be compared to the original, active toxin using a variety of methodologies, including animal models and bioassays.

In a typical approach, the material to be stabilized (e.g., lyophilized salt free toxin) is weighed into 150 ml plastic bottles, each containing 600 mg of toxin. Approximately 800 ml of pure deionized water is allowed to chill in the freezer until ice crystals begin to form. The beaker of pure water is placed in an ice bath and ozonated by bubbling $O_3$ from an ozone generator connected to an $O_2$ source. Measurements of OD are taken at 260 nm using a 1 cm light path until an $OD_{260}$ of 2.0 is achieved.

Sixty ml of ice cold ozonated pure water is added to each bottle containing 600 mg of toxin, resulting in a 1 percent solution (a concentration of 10 mg/ml). While waiting for the powder to dissolve, the bottles are stored in the freezer and ice crystals are again allowed to form. Once in solution, the bottles are placed in an ice bath where each bottle is ozonated for 30 seconds by bubbling ozone into the solution. Ten bottles are done at one time, such that each bottle is ozonated for 30 seconds every five minutes. This is done to maintain an effective level of $O_3$ and is continued for seven hours.

Periodic testing is done by injecting mice with the toxin suspension and monitoring the time to death. When the mice no longer die (after seven hours ozonation) all disulfide bonds have been broken, and the material has been effectively converted from an active toxin to an atoxic toxoid.

It has been noted that if the original ozonated protein solution is maintained at 4° C. for 24 hours and, no further ozonation is carried out, the disulfide bonds are likely not going to be broken, and the solution will remain toxic and able to kill mice. Also, when bacterial or viruses suspensions are added to ozonated water as prepared above, there is immediate 6–8 log kill. Since bacterial and viral kill appears to occur well before oxidation of proteins, ozonated water prepared in this manner can be used to treat protein-containing formulations (e.g., monoclonal antibody preparations) in order to inactive any remaining animal viruses without damaging the antibody itself by breaking critical disulfide bonds.

The oxidized (or stabilized) toxin polypeptide can be compared to the native alpha neurotoxin in a number of respects. It is found that the former is atoxic is mice, while the latter retains full toxicity. The molecular weights as measured on SDS gels are 7380 daltons for both the primary neurotoxin and the resultant oxidized peptide. The isoelectric point as measured by iso-electric focusing gels varies substantially because of the breaking (or stabilized failure to form) of the five disulfide bonds creating a net charge change of ten. The isoelectric point is the pH at which a protein migrates to in an ampholyte solution (continuous pH gradient) to which a current is applied. The primary alpha neurotoxin and resultant oxidized peptide also show separate peaks when measured by HPLC and FPLC.

While a preferred embodiment of the present invention has been described, it should be understood that various changes, adaptations and modifications may be made therein without departing from the spirit of the invention and the scope of the appended claims.

---

What is claimed is:

1. A method for preparing a bioactive polypeptide in an inactivated form, the method comprising the step of treating the polypeptide with ozone under conditions suitable to oxidize any disulfide bonds in order to form corresponding pairs of cysteic acid residues, and to then stabilize the resultant cysteic acid residues and prevent the reformation of disulfide bonds, wherein the inactivated bioactive polypeptide retains one or more properties selected from the group consisting of immunogenicity and anti-viral activity.

2. A method according to claim 1 wherein the bioactive polypeptide is selected from the group consisting of toxins affecting the presynaptic neurojunction, toxins affecting the postsynaptic neurojunction, toxins affecting ion channels, and toxins that damage the cell membrane.

3. A method according to claim 2 wherein the toxins affecting the presynaptic neurojunction toxins are selected from the group consisting of notexin, β-bungarotoxin, crotoxin, taipoxin, textilotoxin and α-latrotoxin.

4. A method according to claim 2 wherein the toxins affecting the postsynaptic neurojunction are selected from the group consisting of α-conotoxins, α-cobrotoxin, erabutoxin, α-cobratoxin and α-bungarotoxin.

5. A method according to claim 2 wherein the toxins affecting ion channels are selected from the group consisting of dendrotoxins, scorpion toxins, m-conotoxins, and sea anemone toxins.

6. A method according to claim 2 wherein the toxins that damage the cell membrane are membrane-damaging toxin selected from the group consisting of myotoxins, cardiotoxins, mellitin, and phospholipases.

7. A method according to claim 1 wherein the bioactive polypeptide is selected from the group consisting of protein hormones and enzymes.

8. A method according to claim 7 wherein the bioactive polypeptide is a protein hormone selected from the group consisting of oxytocin, arginine vasopressin, insulin, growth hormone and calcitonin.

9. A method according to claim 7 wherein the bioactive polypeptide is an enzyme selected from the group consisting of ribonuclease, lysozyme, chymotrypsin, trypsin, elastase, and papain.

10. A method according to claim 1, wherein the composition is suitable for parenteral administration to a host.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (ix) FEATURE:
      (D) OTHER INFORMATION:N represents the nucleoside
         inosine wherever it appears in the sequence (xi) SEQUENCE DESCRIPTION: SEQ ID NO: 1:

GGNCANGTNT GYTAYACNAA RACNTGGTGY GANGCNTTNT G      41

(2) INFORMATION FOR SEQ ID NO: 2:

(i) SEQUENCE CHARACTERISTICS:
      (A) LENGTH: 21 base pairs

-continued

```
        (B) TYPE: nucleic acid
        (C) STRANDEDNESS: single
        (D) TOPOLOGY: linear (xi) SEQUENCE DESCRIPTION:  SEQ ID NO: 2:

GAGTTAGCTC ACTCATTAGG C                                               21

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION:  SEQ ID NO: 3:

ATTTTCATTC GCCATTCAGG C                                               21

(2) INFORMATION FOR SEQ ID NO: 4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION:  SEQ ID NO: 4:

GGATCCGAAT TCACG ATG ATA AGA TGC TTC ATA ACA                          36
Met Ile Arg Cys Phe Ile Thr
1               5

(2) INFORMATION FOR SEQ ID NO: 5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (iv) ANTI-SENSE:  yes (xi) SEQUENCE DESCRIPTION:  SEQ ID NO: 5:

CCTAGGGAAT TCTTATCA AGG ACG TTT GCG TGT TGG                           36
Pro Arg Lys Arg Thr Pro
1               5
```